United States Patent [19]

Foguet et al.

[11] Patent Number: 4,767,767
[45] Date of Patent: Aug. 30, 1988

[54] 2-PYRROLIDINYLETHYL-2-(7-TRI-FLUOROMETHYL-4-QUINOLYL-AMINOBENZOATE HAVING ANALGESIC, ANTIPYRETIC AND ANTI-INFLAMMATORY ACTIVITIES

[75] Inventors: Rafael Foguet, Barcelona; Ernesto Forné; José Ortiz; Aurelio Sacristán, all of Barcelona, Spain

[73] Assignee: Ferrer Internacional S.A., Barcelona, Spain

[21] Appl. No.: 59,911

[22] Filed: Jul. 17, 1987

Related U.S. Application Data

[63] Continuation of Ser. No. 860,687, May 2, 1986, abandoned, which is a continuation of Ser. No. 492,161, May 6, 1983, abandoned.

[30] Foreign Application Priority Data

Jun. 5, 1982 [ES] Spain ..................................... 512605
Jun. 18, 1982 [ES] Spain ..................................... 514341

[51] Int. Cl.$^4$ .................... A61K 31/47; A61K 31/55; C07D 215/44; C07D 405/12
[52] U.S. Cl. .................................... 514/313; 514/212; 514/314; 540/597; 546/161
[58] Field of Search ................. 546/161; 514/313, 314

[56] References Cited

U.S. PATENT DOCUMENTS 3,910,922 10/1975 Allais et al. ........................ 546/161

FOREIGN PATENT DOCUMENTS 1234490 3/1971 United Kingdom .
1462676 1/1977 United Kingdom .

OTHER PUBLICATIONS

Alais et al, Chimie Therapeutique No. 2, 1973, pp. 154–168.

Primary Examiner—Robert Gerstl
Assistant Examiner—Cecilia Shen
Attorney, Agent, or Firm—Michael J. Striker

[57] ABSTRACT 2-amino-benzoic acid derivatives, method for making the same as well as its use for therapeutical purposes are proposed. The general formula of 2-amino-benzoic acid derivatives is

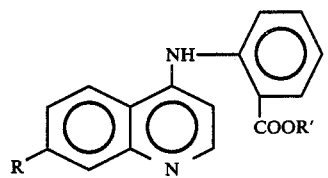

wherein
R represents chlorine or trifluoromethyl,
R' is of general formula

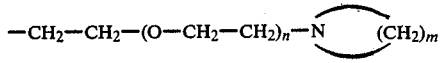

wherein n=0 or 1, m=4, 5, 6, 2-tetrahydropyranyl-methyl, benzyloxymethyl, benzoyloxymethyl of 1(3H)-isobenzofuranone-3-yl.

The compounds show an outstanding analgesic and anti-inflammatory activity and a low toxicity.

2 Claims, No Drawings

2-PYRROLIDINYLETHYL-2-(7-TRI-FLUOROMETHYL-4-QUINOLYL-AMINOBENZOATE HAVING ANALGESIC, ANTIPYRETIC AND ANTI-INFLAMMATORY ACTIVITIES

This is a continuation of application Ser. No. 860,687 filed May 2, 1986, now abandoned, which is a continuation of Ser. No. 492,161, filed May 6, 1983, now abandoned.

BACKGROUND OF THE INVENTION

The present invention relates to 2-amino-benzoic acid derivatives having general formula (I):

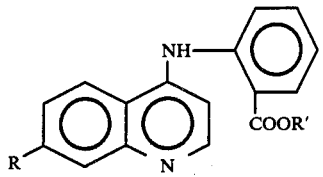

wherein R is chlorine or trifluoromethyl; R' is of general formula

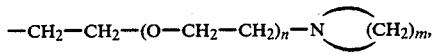

wherein n=0 or 1 and m=4, 5, 6, 2-tetrahydropyranylmethyl, benzyloxymethyl, benzoyloxymethyl and 1(3H)-isobenzofuranone-3-yl; and to their non-toxic addition salts. Moreover, the present invention is concerned with a process for producing 2-amino-benzoic acid derivatives, in particular 2-amino-benzoic acid derivatives of the above general formula wherein R' is

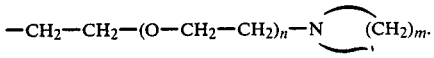

The compounds of the above general formula, especially those compounds in which R' is

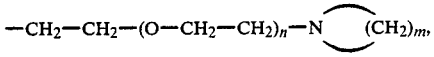

are pharmacologically active having a remarkable analgesic and anti-inflammatory activity, and a low toxicity. Accordingly, these compounds, mixed with suitable carriers, can be administered orally in form of tablets, capsules, syrup, solution, etc., by injection or rectally wherein a daily dosage ranging from 200 to 1000 mg is used.

The compounds show an outstanding analgesic activity, especially upon oral application versus the brewer's yeast test in rat as described by Winter et al. (J. Pharm. Exp. Ther., 150(1), 165–171, 1965). Also these compounds have shown anti-inflammatory activity especially upon oral application versus the Carrageenin test in rats as described by Winter et al. (Proc. Soc. Exp. Biol. Med., 111, 544–547, 1962). The results for the analgesic evaluation are expressed as $ED_{50}$ and those for the anti-inflammatory evaluation expressed as the activity rate observed on administering the compounds at a dose of 5 mg/kg. All these results are comparatively shown over acetylsalicylic acid, antrafenine, floctafenine and glafenine in table 1.

TABLE 1

| Compound (as free base) | R | R' | Analgesic activity $ED_{50}$(mg/kg) | Antiinflammatory activity (%) |
|---|---|---|---|---|
| Example 1 | Cl | —CH$_2$—CH$_2$—N⟨(CH$_2$)$_4$⟩ | 38 | 35,6 |
| Example 2 | CF$_3$ | —CH$_2$—CH$_2$—N⟨(CH$_2$)$_4$⟩ | 2,9 | 38,0 |
| Example 3 | Cl | —CH$_2$—CH$_2$—N⟨(CH$_2$)$_5$⟩ | 67 | 23,1 |
| Example 4 | CF$_3$ | —CH$_2$—CH$_2$—N⟨(CH$_2$)$_5$⟩ | 3,0 | 23,2 |
| Example 5 | Cl | —CH$_2$—CH$_2$—N⟨(CH$_2$)$_6$⟩ | 5,4 | 17,3 |
| Example 6 | CF$_3$ | —CH$_2$—CH$_2$—N⟨(CH$_2$)$_6$⟩ | 7,0 | 27,9 |
| Example 7 | Cl | —CH$_2$—CH$_2$—O—CH$_2$—CH$_2$—N⟨(CH$_2$)$_4$⟩ | 18,5 | 5,1 |
| Example 8 | CF$_3$ | —CH$_2$—CH$_2$—O—CH$_2$—CH$_2$—N⟨(CH$_2$)$_4$⟩ | 14,7 | 26,2 |
| Example 9 | Cl | —CH$_2$—CH$_2$—O—CH$_2$—CH$_2$—N⟨(CH$_2$)$_5$⟩ | 21,7 | 33,2 |
| Example 11 | Cl | —CH$_2$—CH$_2$—O—CH$_2$—CH$_2$—N⟨(CH$_2$)$_6$⟩ | 13,3 | 21,2 |

TABLE 1-continued

| Compound (as free base) | R | R' | Analgesic activity ED50(mg/kg) | Antiinflammatory activity (%) |
|---|---|---|---|---|
| Example 12 | CF3 | —CH2—CH2—O—CH2—CH2—N⟨(CH2)6⟩ | 6,6 | 28,8 |
| Example 14 | Cl | —CH2—⟨(CH2)4/O⟩ | 22 | 19,5 |
| Example 15 | CF3 | —CH2—⟨(CH2)4/O⟩ | 9,3 | 26,1 |
| Example 16 | Cl | —CH2—O—CH2—Ph | 6,3 | 27,7 |
| Example 17 | CF3 | —CH2—O—CH2—Ph | 64,5 | 30,5 |
| Example 18 | Cl | —CH2—O—CO—Ph | 82,5 | 31,0 |
| Example 19 | CF3 | —CH2—O—CO—Ph | 3,8 | 30,5 |
| Example 20 | Cl | phthalide group | 71 | 26,2 |
| Example 21 | CF3 | phthalide group | 26 | 38,4 |
| Acetylsalycilic acid | | | 73 | 23,2 |
| Antrafenine | | | 43 | 3,6 |
| Floctafenine | | | 2,2 | 21,6 |
| Glafenine | | | 26,5 | 25,6 |

Moreover, the above compounds have shown a low toxicity which makes them useful in therapy. $LD_{50}$ for some of the most active compounds are comparatively shown over glafenine in table 2. Evaluation was made according to the method by Reed-Muench as modified by Pizzi (Human & Biology, 22(3), 151–190, 1950) by oral administration to mice.

TABLE 2

| Compound (as free base) | R | R' | LD50 (mg/kg) |
|---|---|---|---|
| Example 1 | Cl | —CH2—CH2—N⟨(CH2)4⟩ | 2000 |
| Example 2 | CF3 | —CH2—CH2—N⟨(CH2)4⟩ | 630 |
| Example 3 | Cl | —CH2—CH2—N⟨(CH2)5⟩ | >2000 |
| Example 4 | CF3 | —CH2—CH2—N⟨(CH2)5⟩ | 635 |
| Example 16 | Cl | —CH2—O—CH2—Ph | >8000 |
| Glafenine | | | 2100 |

Compounds of the present invention mixed with pharmaceutically acceptable carriers can be administered by oral application in form of tablets, capsules, syrup, solution, etc., by injection and by rectal application, at daily doses ranging from 200 to 1000 mg.

The compound (I) of the invention can be made in various ways.

(a) Reaction of a base compound having the general formula (II):

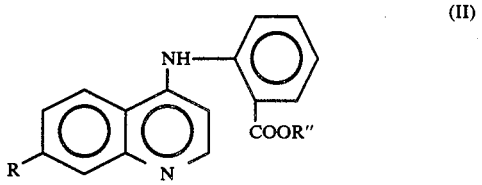

(II)

with a compound having the general formula (III): X—R'. wherein
R and R' is as outlined with formula I
R" is $C_1$–$C_4$-alkyl or hydrogen
X is hydroxy or halogen In those cases in which compound (II) has ester-like nature, i.e. R" is a $C_1$–$C_4$ alkyl rest, preferable methyl, the reaction is carried out with compound (III) wherein X is OH; the reaction is properly catalyzed by sodium or sodium hydride and completed at boiling temperature in an aromatic solvent, such as toluene. This reaction is preferably applied when R' is

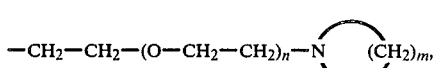

wherein n and m are as defined above, or when R' is 2-tetrahydropyranylmethyl.

On the other hand, in those cases in which R" is hydrogen, the reaction is carried out with compound (III) wherein X is a halogen atom, selected between bromine and chlorine. This reaction is preferably applied when R' is benzyloxymethyl, benzoyloxymethyl and 1(3H)-isobenzofuranone-3-yl. Due to the insolubility of the acids (II, R"=H) in most of organic solvents, even polar aprotic solvents, as well as their inorganic salts, the use of organic salts, such as triethylamine, tri-n-butylamine or the like, is preferred which makes solubilization to be attained and consequently facilitating reaction to a great extent. The reaction then occurs under a highly-yielded step by using at room temperature hexamethylphosphorotriamide or N,N-dimethylformamide as solvent.

Compound (III), wherein X is OH and R' is

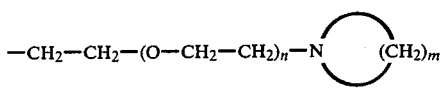

wherein n is 0 and m is as defined above, are obtained according to the methods described by A. Lespagnol and J. Desprey (Bull. Soc. Chim. France, 3, 606–610, 1961). As for respective analogs with n=1, we have simplified their preparation by modifying the method by H. Najer et al. (Bull. Soc. Chim. France, 3, 355–359, 1958), since it has been found out that such intermediates are advantageously obtained by reacting commercially available 2-(2-chloroethoxy)ethanol and the corresponding cyclic amine, thus avoiding under pressure laboratory operations.

(b) Reaction of isatoic anhydride with intermediate alcohols of compound (IV), followed by subsequent alkylation with the corresponding 4-chloro-quinoleines (IV), leads to the compounds of general formula (I) in accordance with the following equation:

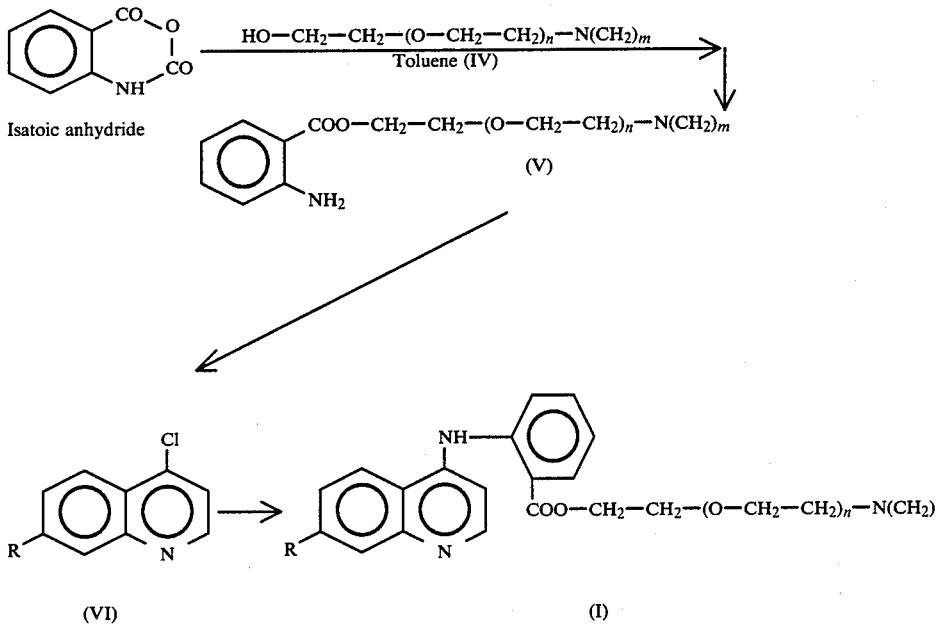

In the above diagram, R, n and m, for formulas (IV), (V) and (VI), are as defined above in connection with formula (I). The first reaction is suitably conducted in an aromatic solvent, for example, toluene, under the boiling point of same. The second reaction is suitably conducted in an acid aqueous solution, under the boiling point of same.

These reactions provide an industrially useful process since the isatoic anhydride is evidently a commercially available starting product.

EXAMPLES

A number of examples will now be described in non-limitative manner to illustrate the invention and naturally larger quantities than those indicated can be used in industry.

EXAMPLE 1

2-Pyrrolidinylethyl 2-(7-chloro-4-quinolyl)aminobenzoate

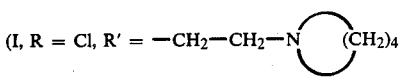

A mixture containing 18.76 g of methyl 2-(7-chloro-4-quinolyl)-aminobenzoate (II, R=Cl, R"=CH$_3$) (A. Allais et al: "Chim. Ther.", 2, 65–70, 1966) and 10.28 g of 1-(2-hydroxyethyl)-pyrrolidine in 150 ml of toluene is heated under oil-bath till distilling about 30 ml of solvent; it is allowed to cool down to 50° C. and a small scrap of clean sodium is added. Temperature is gradually increased in order to distill the formed methanol while substituting the toluene which is also removed. Eight hours later and after having added, at identical intervals, two further scraps of sodium, the mixture is subjected to reflux for 2 hours; it is observed by thin-layer chromatography (silicagel; eluent, chloroform-methanol 9:1) that the transesterification is just complete. The toluene is evaporated under vacuum, the residue is dissolved in 500 ml of chloroform and then filtered off. The organic extract is washed with water, 10% sodium hydroxide solution, and water again. After the solvent is evaporated, the solid residue weights 22.1 g (yield: 94%). By recrystallization in diisopropyl ether, 14.5 g (yield: 62%) of pale-yellow solid are obtained with m.p. 102°–104° C. and elemental analysis correct.

IR Spectrum (KBr), cm⁻¹: 3280, 3000–2740, 1670, 1600, 1570, 1525, 1450, 1370, 1245, 1160, 1080, 875, 860, 745.

EXAMPLE 2

2-Pyrrolidinylethyl
2-(7-trifluoromethyl-4-quinolyl)aminobenzoate

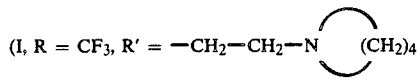

(I, R = CF$_3$, R' = —CH$_2$—CH$_2$—N(CH$_2$)$_4$)

By treating 19.5 g of methyl 2-(7-trifluoromethyl-4-quinolyl)aminobenzoate (II, R=CF$_3$, R''=CH$_3$) and 9.59 g of 1-(2-hydroxyethyl)pyrrolidine in 145 ml of toluene and in the presence of sodium as described in Example 1, 19.2 g of a crude material are isolated. Purification through silicagel, elution with a mixture of highly polar chloroform-methanol, and treatment of the product thus purified with hexane, it yields 11.6 g (56%) of white-yellowish solid with m.p. 63°–65° C. and elemental analysis C, H, N and F correct.

IR Spectrum (KBr), cm⁻¹: 3400, 3240, 3000–2740, 1670, 1595, 1580, 1530, 1455, 1320, 1250, 1155, 1120, 905, 750.

EXAMPLE 3

2-Piperidinylethyl-2-(7-chloro-4-quinolyl)aminobenzoate

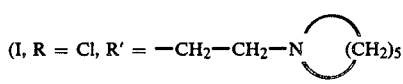

(I, R = Cl, R' = —CH$_2$—CH$_2$—N(CH$_2$)$_5$)

By treating 15.54 g of methyl 2-(7-chloro-4-quinolyl)aminobenzoate (II, R=Cl, R''=CH$_3$), and 10.0 g of 1-(2-hydroxyethyl)piperidine in 100 ml of toluene and in the presence of sodium as described in Example 1, 17.0 g of a crude material are isolated. By recrystallization in diisopropyl ether and active carbon, 12.8 g (yield: 63%) of pale-yellow solid are obtained with m.p. 100°–101° C. and elemental analysis correct.

IR Spectrum (KBr), cm⁻¹: 3300, 3030, 2920, 2900–2760, 1680, 1600, 1575, 1520, 1450, 1250, 1160, 1065, 865, 740.

EXAMPLE 4

2-Piperidinylethyl
2-(7-trifluoromethyl-4-quinolyl)aminobenzoate

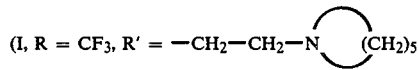

(I, R = CF$_3$, R' = —CH$_2$—CH$_2$—N(CH$_2$)$_5$)

By treating 17.31 g of methyl 2-(7-trifluoromethyl-4-quinolyl)aminobenzoate (II, R=CF$_3$, R''=CH$_3$) and 9.56 g of 1-(2-hydroxyethyl)-piperidine in 130 ml of toluene and in the presence of sodium as described in Example 1, 17.9 g of a crude material are isolated. Purification through silicagel and recrystallization in diisopropyl ether enables to isolate 13.3 g (yield: 60%) of white solid with m.p. 78°–80° C. and elemental analysis C, H, N, F correct.

IR Spectrum (KBr), cm⁻¹: 3440, 3320, 3000–2700, 1695, 1605, 1580, 1530, 1380, 1325, 1255, 1150, 1130, 825, 740.

EXAMPLE 5

2-Homopiperidinylethyl
2-(7-chloro-4-quinolyl)aminobenzoate

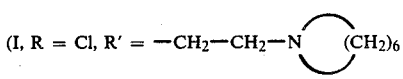

(I, R = Cl, R' = —CH$_2$—CH$_2$—N(CH$_2$)$_6$)

By treating 18.76 of methyl 2-(7-chloro-4-quinolyl)aminobenzoate (II, R=Cl, R''=CH$_3$) and 12.72 of 1-(2-hydroxyethyl)homopiperidine in 150 ml of toluene and in the presence of sodium as described in Example 1, 22.07 g of a crude material are isolated. By recrystallization in diisopropyl ether, 15.5 g (yield: 61%) of a yellowish solid are obtained with m.p. 76.5–78° C. and elemental analysis C, H, N, Cl correct.

IR Spectrum (KBr), cm⁻¹: 3280, 3000–2760, 1675, 1605, 1570, 1520, 1450, 1320, 1240, 1160, 1080, 875, 745.

EXAMPLE 6

2-Homopiperidinylethyl
2-(7-trifluoromethyl-4-quinolyl)aminobenzoate

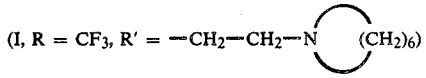

(I, R = CF$_3$, R' = —CH$_2$—CH$_2$—N(CH$_2$)$_6$)

By treating 17.31 g of methyl 2-(7-trifluoromethyl-4-quinolyl)aminobenzoate (II, R=CF$_3$, R''=CH$_3$), 10.5 g of 1-(2-hydroxyethyl)homopiperidine in 130 ml of toluene and in the presence of sodium as described in Example 1, 20.6 g of a crude material are isolated. The recrystallization in diisopropyl ether enables to isolate 13.7 g (yield: 60%) of a whitish solid with m.p. 72°–75° C. and elemental analysis C, H, N, F correct.

IR spectrum (KBr), cm⁻¹: 3420, 3000–2790, 1680, 1605, 1580, 1530, 1450, 1380, 1320, 1250, 1155, 1025, 900, 745.

EXAMPLE 7

2-(2-Pyrrolidineethoxy)ethyl
2-(7-chloro-4-quinolyl)aminobenzoate

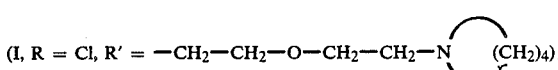

(I, R = Cl, R' = —CH$_2$—CH$_2$—O—CH$_2$—CH$_2$—N(CH$_2$)$_4$)

By treating 18.76 g of methyl 2-(7-chloro-4-quinolyl)aminobenzoate (II, R=Cl, R''=CH$_3$) and 14.14 g of 2-(2-pyrrolidineethoxy)ethanol in 150 ml of toluene and in the presence of sodium as described in Example 1, 16.2 g of a crude material are isolated. Purification through silicagel and crystallization in hexane enables to isolate 10.81 g (yield: 41%) of a yellow solid with m.p. 60°–63° C. and elemental analsysis C, H, N, Cl correct.

IR Spectrum (KBr), cm⁻¹: 3290, 3000–2890, 1670, 1610, 1575, 1525, 1455, 1250, 1085, 860, 745.

EXAMPLE 8

2-(2-Pyrrolidineethoxy)ethyl
2-(7-trifluoromethyl-4-quinolyl)aminobenzoate

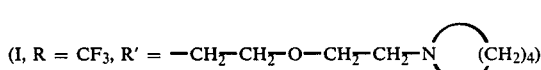

(I, R = CF$_3$, R' = —CH$_2$—CH$_2$—O—CH$_2$—CH$_2$—N(CH$_2$)$_4$)

By treating 17.31 g of methyl 2-(7-trifluoromethyl-4-quinolyl)aminobenzoate (II, R=CF$_3$, R''=CH$_3$), and 11.78 g of 2-(2-pyrrolidineethoxy)ethanol in 150 ml of toluene and in the presence of sodium as described in Example 1, 13.9 g of a crude material are isolated under nitrogen atmosphere. Purification through silicagel and crystallization in hexane enables to isolate 6.95 g (yield: 30%) of a white solid with m.p. 58°-61° C. and elemental analysis C, H, N, F correct.

IR Spectrum (KBr), cm$^{-1}$: 3400, 3240, 3000-2780, 1675, 1595, 1585, 1530, 1455, 1380, 1325, 1250, 1160, 1115, 750.

EXAMPLE 9

2-(2-Pyrrolidineethoxy)ethyl 2-(7-chloro-4-quinolyl)-aminobenzoate

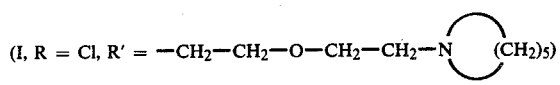

By treating 18.76 g of methyl 2-(7-chloro-4-quinolyl)aminobenzoate (II, R=Cl, R''=CH$_3$), and 15.38 g of 2-(2-piperidineethoxy)ethanol in 150 ml of toluene and in the presence of sodium as described in Example 1, 20.32 g of a resinuous crude material are isolated. Subsequent treatment with 50 ml of hexane and decantation results in a solid material which is recrystallized from diisopropyl ether. 12.2 g (yield: 45%) of a yellowish solid are obtained with m.p. 75°-79° C. and elemental analysis C, H, N, Cl correct.

IR Spectrum (KBr), cm$^{-1}$: 3440, 3240, 3000-2660, 1675, 1600, 1580, 1530, 1450, 1375, 1255, 1130, 1085, 950, 745.

EXAMPLE 10

2-(2-Piperidineethoxy)ethyl 2-(7-trifluoromethyl-4-quinolyl)aminobenzoate

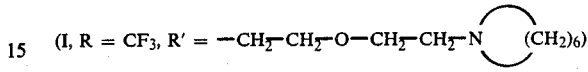

By treating 17.31 g of methyl 2-(7-trifluoromethyl-4-quinolyl)aminobenzoate (II, R=CF$_3$, R''=CH$_3$), and 15.4 g of 2-(2-piperidineethoxy)ethanol in 150 ml of toluene and in the presence of sodium as described in Example 1, 22.1 g of a crude material are isolated. Subsequent treatment with hexane (50 ml) and recrystallization of the insolute in diisopropyl ether, 10.4 g (yield: 43%) of a yellowish solid are obtained with m.p. 81°-83° C. and elemental analysis C, H, N, F correct.

IR Spectrum (KBr), cm$^{-1}$: 3290, 3000-2700, 1675, 1610, 1580, 1530, 1455, 1250, 1150, 745.

EXAMPLE 11

2-(2-Homopiperidineethoxy)ethyl 2-(7-chloro-4-quinolyl)aminobenzoate

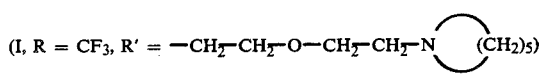

By treating 18.76 g of methyl 2-(7-chloro-4-quinolyl)aminobenzoate (II, R=Cl, R''=CH$_3$) and 16.63 g of 2-(2-homopiperidineethoxy)ethanol in 150 ml of toluene and in the presence of sodium, as described in Example 1, 29.3 g of a resinous crude material are isolated. Subsequent treatment in 50 ml of hexane and decantation results in a solid material which is consecutively recrystallized in hexane and diisopropyl ether. 13.3 g (yield: 49%) of a yellowish solid are obtained with m.p. 62°-64° C. and elemental analysis C, H, N, Cl correct.

IR Spectrum (KBr), cm$^{-1}$: 3240, 3000-2700, 1675, 1600, 1570, 1520, 1445, 1245, 1080, 875, 740.

EXAMPLE 12

2-(2-Homopiperidineethoxy)ethyl 2-(7-trifluoromethyl-4-quinolyl)aminobenzoate

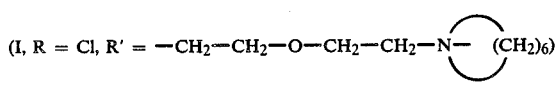

By treating 17.31 g of methyl 2-(7-trifluoromethyl-4-quinolyl)aminobenzoate (II, R=CF$_3$, R''=CH$_3$), 13.85 g of 2-(2-homopiperidineethoxy)ethanol, 150 ml of toluene and in the presence of sodium, as described in Example 1, 20.3 g of a resinous crude material are isolated. Subsequent crystallization in n-pentane and diisopropyl ether yields 12.1 g (47.5%) of a white-yellowish solid with m.p. 53.56° C. and elemental analysis C, H, N, F correct.

IR Spectrum (KBr), cm$^{-1}$: 3260, 3000-2700, 1670, 1595, 1580, 1520, 1445, 1375, 1315, 1240, 1155, 1105, 740.

EXAMPLE 13

(a) 2-(2-Homopiperidineethoxy)ethanol

A mixture, under stirring, containing 59.81 g of hexamethylenimine and 50.66 g of sodium bicarbonate in 1 liter of absolute ethanol, is allowed to drip 56.06 g of 2-(2-chloroethoxy)ethanol, and then subjected to reflux for 24 hours. It is cooled, the insoluble is filtered off, the ethanol is distilled under vacuum and the residue (82.1 g) is dissolved in ethyl ether, filtered again and, under cooling, 55 ml of hydrochloride acid (g) 10N ethanolic solution are added. After 30 minutes the precipitated hydrochloride is filtered and dried, thus obtaining 80 g (yield: 70%) of a white solid, m.p. 96°-99° C. and analysis correct.

The hydrochloride thus obtained in 225 ml of water is brought to highly basic pH by addition of concentrated NH$_4$OH; it is extracted with methylene chloride, dried and solvent is evaporated. By distillation under vacuum of the residue, 68.5 g (yield: 61%) of a colorless liquid are obtained with b.p. 125° C./2.5 torr, n$_D^{20}$=1.4819.

IR Spectrum (film), cm$^{-1}$: 3400, 3000-2600, 1450, 1350, 1320, 1130, 1060, 890.

By operating as described in (a) for 2-(2-pyrrolidine ethoxy)ethanol and 2-(2-(2-piperidineethoxy)ethanol, both compounds are obtained with the following features:

(b) 2-(2-pyrrolidineethoxy)ethanol: n$_D^{20}$=1.4695; m.p. (HCl), 104°-108° C. IR Spectrum (film), cm$^{-1}$: 3400, 3000-2700, 1460, 1350, 1125, 1060, 880.

(c) 2-(2-piperidineethoxy)ethanol: n$_D^{20}$=1.4765; m.p. (HCl), 114°-118° C. IR Spectrum (film), cm$^{-1}$: 3500, 3000-2600, 1440, 1340, 1300, 1260, 1130, 1050, 1030, 850, 750.

EXAMPLE 14

2-Tetrahydropyranylmethyl
2-(7-chloro-4-quinolyl)aminobenzoate

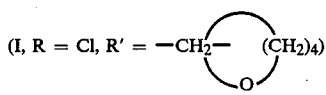

(I, R = Cl, R' = —CH$_2$— (CH$_2$)$_4$)

By treating 15.4 g of methyl 2-(7-chloro-4-quinolyl)aminobenzoate (II, R=Cl, R''=CH$_3$), 8.46 g of 2-hydroxymethyltetrahydropyran, 125 ml of toluene and in the presence of sodium, as described in Example 1, 19.8 g of a crude material are isolated. This material is dissolved in 250 ml of diisopropyl ether and 7 ml of hydrochloric acid (g) 10N ethanolic solution are added under cooling in water-ice bath. After 15 minutes the precipitated hydrochloride is filtered off, dried (19.45 g; 91%) and recrystallized in acetonitrile. 14.34 g (yield: 67%) of the hydrochloride—yellow solid—are obtained with m.p. 187°–187.5° C. and elemental analysis C, H, N, Cl correct.

The above hydrochloride, dissolved in 300 ml of warm water, is brought to highly basic pH with concentrated NH$_4$OH solution. The resinous solid thus obtained is ground with diisopropyl ether and filtered off. After drying, a white solid weighing 11.8 g (yield: 60%) is obtained with m.p. 93°–94° C. and elemental analysis C, H, N, Cl correct.

IR Spectrum (Kbr), cm$^{-1}$: 3260, 3000–2800, 1680, 1605, 1570, 1520, 1445, 1250, 1080, 745.

EXAMPLE 15

2-Tetrahydropyranylmethyl
2-(7-trifluoromethyl-4-quinolyl)aminobenzoate

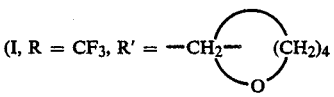

(I, R = CF$_3$, R' = —CH$_2$— (CH$_2$)$_4$)

By treating 16.97 g of methyl 2-(7-trifluoromethyl-4-quinolyl aminobenzoate (II, R=CF$_3$, R''=CH$_3$), 8.42 g of 2-hydroxymethyltetrahydropyran, 125 ml of toluene, and in the presence of sodium, as described in Example 1, 18.73 g of a crude material are isolated. The hydrochloride is formed as described in the above example and recrystallized in acetonitrile, thus obtaining 13.1 g (yield: 62%) of a yellow solid, m.p. 217°–221° C. and elemental analysis C, H, N, Cl correct. The base obtained by neutralization is dried and ground with hexane. Yield: 10.97 g (52%) of a white solid with m.p. 76°–80° C. and elemental analysis C, H, N, F correct.

IR Spectrum (KBr), cm$^{-1}$: 3260, 2940, 2850, 1690, 1610, 1580, 1530, 1455, 1325, 1250, 1150, 1130, 750.

EXAMPLE 16

Benzyloxymethyl
2-(7-chloro-4-quinolyl)aminobenzoate (I, R=Cl, R''=—CH$_2$—O—CH$_2$—Ph)

To a suspension of 14.94 g of 2-(7-chloro-4-quinolyl)aminobenzoic acid (II, R=Cl, R''=H) in 300 ml of hexamethylphosphorotriamide, 6.32 g of dry triethylamine are added and the mixture is stirred till the whole acid turns into solution. Then 9.79 g of benzylchloromethyl ether are added by stirring for 48 hours at room temperature. The mixture is poured onto 1.5 liters of water, then allowed to stand for a few hours, filtered and repeatedly washed with water. After drying (20.5 g), it is recrystallized from a acetonitrile thus obtaining 18.4 g (yield: 88%) of a whitish solid, m.p. 131°–134° C. and elemental analysis C, H, N, Cl correct.

IR Spectrum (KBr), cm$^{-1}$: 3300, 3020, 2950, 1690, 1610, 1565, 1445, 1250, 1150, 1040, 940, 735.

EXAMPLE 17

Benzyloxymethyl
2-(7-trifluoromethyl-4-quinolyl)aminobenzoate (I, R=CF$_3$, R'=—CH$_2$—O—CH$_2$—Ph)

By treating 10.3 g of 2-(7-trifluoromethyl-4-quinolyl)aminobenzoic acid (II, R=CF$_3$, R''=H) in 200 ml of hexamethylphosphorotriamide, 3.93 g of triethylamine and 6.08 g of benzylchloromethyl ether as described in Example 16, 17.22 g of a crude material are isolated which by recrystallization in acetonitrile yields 10.12 g (72%) of a whitish solid, m.p. 87.5°–89° C. and elemental analysis C, H, N, F correct.

IR Spectrum (KBr), cm$^{-1}$: 3260, 3060–2090, 1685, 1605, 1570, 1530, 1320, 1245, 1150, 1040, 920, 740.

EXAMPLE 18

Benzoyloxymethyl
2-(7-chloro-4-quinolyl)aminobenzoate (I, R=Cl, R'=—CH$_2$—O—CO—Ph)

By treating 11.05 g of 2-(7-chloro-4-quinolyl)aminobenzoic acid (II, R=Cl, R''=H) in 225 ml of hexamethylphosphorotriamide, 4.70 g of triethylamine and 7.90 g of chloromethyl benzoate as described in Example 16, 12.6 g (yield: 70%) are isolated after recrystallization in acetonitrile as a yellowish solid; m.p. 139°–141° C. and elemental analysis C, H, N, Cl correct.

IR Spectrum (KBr), cm$^{-1}$: 3320, 3040–2980, 1740, 1685, 1580, 1520, 1450, 1240, 1150, 1045, 1025, 740, 710.

EXAMPLE 19

Benzoyloxymethyl
2-(7-trifluoromethyl-4-quinolyl)aminobenzoate (I, R=CF$_3$, R'=—CH$_2$—O—CO—Ph)

By treating 10.9 g of 2-(7-trifluoromethyl-4-quinolyl)aminobenzoic acid (II, R=CF$_3$, R''=H) in 200 ml of hexamethylphosphorotriamide, 4.15 g of triethylamine and 7.0 g of chloromethyl benzoate as described in Example 16, 8.4 g (yield: 56%) are isolated after recrystallization in acetonitrile; m.p. 100°–103° C. and elemental analysis C, H, N, F correct.

IR Spectrum (KBr), cm$^{-1}$: 3300, 3040–2980, 1735, 1690, 1580, 1530, 1450, 1325, 1240, 1145, 1040, 975, 745, 710.

EXAMPLE 20

1(3H)-isobenzofuranone-3-yl
2-(7-chloro-4-quinolyl)aminobenzoate

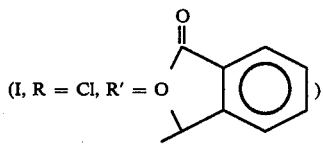

(I, R = Cl, R' = O )

By treating 9.82 g of 2-(7-chloro-4-quinolyl)aminobenzoic acid (II, R=Cl, R''=H) in 200 ml of hexamethylphosphorotriamide, 4.16 g of triethylamine and 8.75 g of 3-bromo-1(3H)-isobenzofuranone as described in Example 16, 15 g are isolated which recrystallization in acetonitrile yields 11.9 g (84%) of a yellow solid, m.p. 213°-215° C. and elemental analysis of C, H, N, Cl correct.

IR Spectrum (KBr), cm⁻¹: 3300, 3040, 1780, 1695, 1610, 1585, 1525, 1455, 1240, 1070, 970, 745.

EXAMPLE 21

1(3H)-isobenzofuranone-3-yl 2-(7-trifluoromethyl-4-quinolyl)aminobenzoate

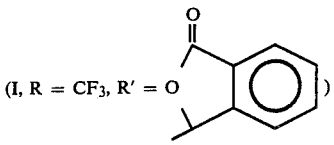

By treating 9.55 g of 2-(7-trifluoromethyl-4-quinolyl)aminobenzoic acid (II, CF₃, R″=H) in 200 ml of hexamethylphosphorotriamide, 3.65 g of triethylamine and 7.69 g of 3-bromo-1(3H)-isobenzofuranone as described in Example 16, 11.3 g (yield: 85%) of a yellow solid are isolated after recrystallization in acetonitrile, m.p. 218°-220° C. and elemental analysis of C, H, N, F correct.

IR Spectrum (KBr), cm⁻¹: 3300, 3010, 1780, 1700, 1580, 1540, 1460, 1360, 1245, 1155, 1125, 980, 750.

EXAMPLE 22

2-Pyrrolidinylethyl, 2-(7-chloro-4-quinolyl)aminobenzoate

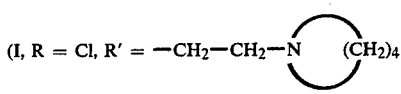

(A) 2-Pyrrolidinylethyl antranilate (V, n=0, m=4):

A mixture with 15.07 g of isatoic anhydride and 7.96 g of 1-(2-hydroxyethyl)pyrrolidine in 150 ml of toluene is subjected to reflux under stirring for 3 hours. Active carbon is added and then filtered off under heating. The toluene is evaporated under reduced pressure, the residue is taken in ethyl ether, the insoluble is filtered off and the organic solution, under cooling, is extracted twice with 75 ml of 6N hydrochloride acid solution. The acid extracts are brought under cooling, to basic pH with concentrated ammonium hydroxide solution and the oil thus separated is extracted with ethyl ether, washed and dried. After the solvent is evaporated, the residue, a yellow oil with $n_D^{20}=1.572$ and elemental analysis correct weights 13.8 g (yield: 85%). It is distillable in ball furnace with b.p. 185°-190° C./10⁻³-10⁻⁴ Torr.

IR Spectrum (film), cm⁻¹: 3470, 3360, 3260, 2880, 2800, 1680, 1610, 1580, 1480, 1450, 1285, 1235, 1150, 1100, 740.

(B) Reaction with 4,7-dichloroquinoleine (VI, R=Cl):

11.71 g of 2-pyrrolidinylethyl antranilate, as described above, and 9.90 g of 4,7-dichloroquinoleine in 50 ml of 2N hydrochloride acid are subjected to reflux under stirring for 3 hours. The mixture is allowed to cool, the insoluble is filtered off, and the filtrate is brought to strongly basic pH with saturated sodium carbonate solution. The separated solid is filtered off, washed repeatedly and dried. 11.5 g (yield: 58%) are obtained by recrystallization with m.p. 102°-104° C. and elemental analysis correct.

IR Spectrum (KBr), cm⁻¹: 3280, 3000-2740, 1670, 1600, 1570, 1525, 1450, 1370, 1245, 1160, 1080, 875, 860, 745.

EXAMPLE 23

2-Pyrrolidinylethyl 2-(7-trifluoromethyl-4-quinolyl)aminobenzoate

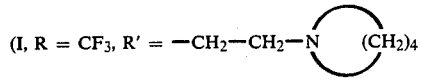

A mixture with 96.2 g of 2-pyrrolidinylethyl antranilate and 95.1 g of 4-chloro-7-trifluoromethylquinoline in 410 ml of 2N hydrochloride acid is subjected to reflux under stirring for 3 hours. 127 g of a whitish solid are obtained according to Example 22. Recrystallization in n-pentane yields 95.3 g (54%) of a white-yellowish solid with m.p. 65°-68° C. and elemental analysis correct.

IR Spectrum (KBr), cm⁻¹: 3400, 3240, 3000-2740, 1670, 1595, 1580, 1530, 1455, 1320, 1155, 1120, 905, 750.

EXAMPLE 24

2-Piperidinylethyl 2-(7-chloro-4-quinolyl)aminobenzoate

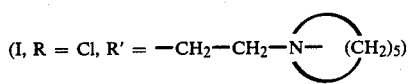

(A) 2-Piperidinylethyl antranilate (V, n=0, m=5):

22.95 g of isatoic anhydride are reacted with 13.59 g of 1-(2-hydroexyl)piperidine in 220 ml of toluene. 20.53 g (yield: 75%) of a yellow oil are isolated according to Example 22; $n_D^{20}=1.567$ and elemental analysis correct. It may be purified by careful distillation in ball furnace at 175°-190° C./10⁻³, 10⁻⁴ Torr.

IR Spectrum (KBr), cm⁻¹: 3480, 3370, 2940, 2790, 1690, 1620, 1590, 1490, 1455, 1290, 1245, 1160, 1105, 750.

(b) Reaction with 4,7-dichloroquinoleine (VI, R=Cl):

12.41 g of 2-piperidinylethyl antranilate (as described above) and 9.90 g of 4,7-dichloroquinoleine in 50 ml of 2N hydrochloride acid are subjected to reflux for 3 hours. As described in Example 22, and by recrystallization in diisopropyl ether, 11.4 g (yield: 56%); m.p. 101°-102° C. and elemental analysis correct.

IR Spectrum (KBr), cm⁻¹: 3300, 3030, 2920, 2900-2760, 1680, 1605, 1575, 1520, 1450, 1250, 1160, 1065, 865, 740.

EXAMPLE 25

2-Piperidinylethyl 2-(7-trifluoromethyl-4-quinolyl)aminobenzoate

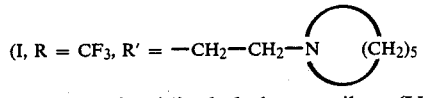

By treating 2-piperidinylethyl antranilate (V, n=0, m=5) (51 g) and 4-chloro-7-trifluoromethylquinoline (47.6 g) as described in Example 22, and by recrystallization in n-pentane, 51.9 g (yield: 57%) are obtained; m.p. 78°-80° C. and elemental analysis correct.

IR Spectrum (KBr), cm⁻¹: 3440, 3320, 3000-2760, 1695, 1605, 1580, 1530, 1380, 1325, 1255, 1150, 1130, 825, 740.

EXAMPLE 26

2-Homopiperidinylethyl 2-(7-chloro-4-quinolyl)aminobenzoate

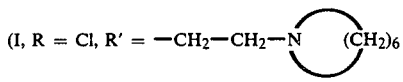

(A) 2-Homopiperidinylethyl antranilate (V, n=0, m=6):

7.54 g of isatoic anhydride are reacted with 5.36 g of 1-(2-hydroxyethyl)-homopiperidine in 100 ml of toluene, 9.46 g of a viscous yellow oil are isolated according to Example 22. By distillation in ball furnace 6.8 g (yield: 70%) of oil are obtained at 180°–195° C./$10^{-3}$, $10^{-4}$ Torr, $n_D^{20}=1.570$ and elemental analysis of C, H, N correct.

IR Spectrum (film), cm$^{-1}$: 3470, 3360, 1680, 1610, 1580, 1480, 1450, 1290, 1240, 1155, 1105, 750, 700.

(B) Reaction with 4,7-dichloroquinoleine (VI, R=Cl):

By treating 2-homopiperidinylethyl antranilate (5.4 g) as above described and 4,7-dichloroquinoline (4.1 g) according to Example 22, and after recrystallization, 5.1 g (yield: 55%) are obtained; m.p. 76.5°–78° C. and elemental analysis correct.

IR Spectrum (KBr), cm$^{-1}$: 3280, 3000–2760, 1675, 1605, 1570, 1520, 1450, 1320, 1240, 1160, 1080, 875, 745.

EXAMPLE 27

2-Homopiperidinylethyl 2-(7-trifluoromethyl-4-quinolyl)aminobenzoate

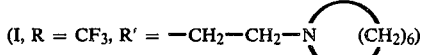

By treating 2-homopiperidinylethyl antranilate (5.40 g) as described in Example 26, and 4-chloro-7-trifluoromethylquinoleine (4.75 g) as described in Example 22, and after recrystallization in diisopropyl ether, 5.4 g (yield: 58%) are obtained; m.p. 72°–75° C. and elemental analysis correct.

IR Spectrum (KBr), cm$^{-1}$: 3420, 3240, 3000–2790, 1680, 1605, 1580, 1530, 1450, 1380, 1320, 1250, 1155, 1025, 900, 745.

EXAMPLE 28

2-(2-Pyrrolidinethoxy)ethyl 2-(7-chloro-4-quinolyl)aminobenzoate

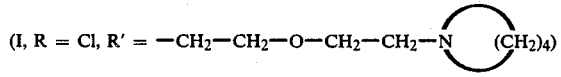

(A) 2-(2-Pyrrolidinethoxy)ethyl antranilate (V, n=1, m=4):

11.0 g of 2-(2-pyrrolidinethoxy)ethanol are reacted with 15.07 g of isatoic anhydride in 170 ml of toluene. 14.5 g (yield: 76%) of a viscous yellow oil are isolated according to Example 22. Then, it is purified by careful distillation in ball furnace at 175°–190° C./$10^{-3}$, $10^{-4}$ Torr, as a heavy oil of $n_D^{20}=1.5589$ and elemental analysis C, H, N, correct.

IR Spectrum (film), cm$^{-1}$: 3460, 3380, 3010–2700, 1685, 1615, 1585, 1485, 1455, 1290, 1245, 1160, 1100, 860, 750.

(B) Reaction of 4,7-dichloroquinoleine (VI, R=Cl):

By treating 2-(2-pyrrolidinethoxy)ethyl antranilate (7.72 g) as described above, and 4,7-dichloroquinoleine (7.01 g) in 24 ml of 2N hydrochloride acid and 115 ml of water under reflux for 3 hours, followed by neutralization with sodium bicarbonate, extraction with methylene chloride and evaporation of solvent, 11.2 g of a material are isolated which after being purified by silicagel column chromatography and crystallization in hexane gives 7.3 g (60%); m.p. 60°–63° C. and elemental analysis correct.

IR Spectrum (KBr), cm$^{-1}$: 3290, 3000–2890, 1670, 1610, 1575, 1525, 1455, 1250, 1085, 860, 745.

EXAMPLE 29

2-(2-Pyrrolidinethoxy)ethyl 2-(7-trifluoromethyl-4-quinolyl)aminobenzoate

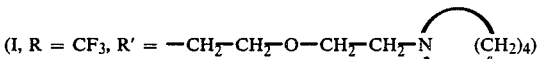

By treating 2-(2-pyrrolidinethoxy)ethyl (7.7 g) as described in Example 28, and 4-chloro-7-trifluoromethylquinoleine (8.2 g) as described in Example 7, 7.8 g (yield: 60%) are obtained; m.p. 58°–61° C. and elemental analysis correct.

IR Spectrum (KBr), cm$^{-1}$: 3400, 3240, 3000–2780, 1675, 1595, 1585, 1530, 1455, 1380, 1325, 1250, 1160, 1115, 750.

EXAMPLE 30

2-(2-Piperidinethoxy)ethyl 2-(7-chloro-4-quinolyl)aminobenzoate

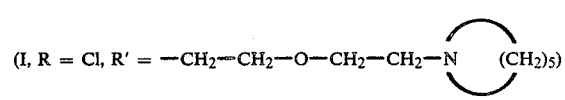

(A) 2-(2-Piperidinethoxy)ethyl antranilate (V, n=1, m=4):

8.2 g of 2-(2-piperidinethoxy)ethanol are reacted with 10.3 g of isatoic anhydride in 120 ml of toluene. 8.22 g (yield: 60%) of a yellow oil are isolated according to Example 22. Then, it is purified by careful distillation in ball furnace at 190°–210° C./$10^{-3}$ Torr, as a viscous yellow oil with $n_D^{20}=1.5528$ and elemental analysis of C, H, N correct.

IR Spectrum (KBr), cm$^{-1}$: 3460, 3360, 3000–2700, 1685, 1615, 1290, 1240, 1155, 1100, 750.

(B) Reaction of 4,7-dichloroquinoleine (VI, R=Cl):

By treating 2-(2-piperidinethoxy)ethyl antranilate (5.85 g) as described above, and 4,7-dichloroquinoleine (5.07 g), it is obtained a solid (yield: 57%) as described in Example 28; m.p. 75°–79° C. and elemental analysis correct.

IR Spectrum (KBr), cm$^{-1}$: 3440, 3240, 3300–2660, 1675, 1600, 1580, 1530, 1450, 1375, 1255, 1130, 1085, 950, 745.

EXAMPLE 31

2-(2-Piperidinethoxy)ethyl 2-(7-trifluoromethyl-4-quinolyl)aminobenzoate

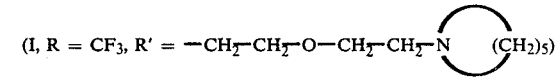

By treating 2-(2-piperidinethoxy)ethyl antranilate (6.12 g) as described in Example 30 and 4-chloro-7-trifluoromethylquinoleine (5.92 g) as described in above examples, it is obtained a solid (yield: 53%); m.p. 81°-83° C. and elemental analysis correct.

IR Spectrum (KBr), cm$^{-1}$: 3290, 3000-2700, 1675, 1610, 1580, 1530, 1455, 1250, 1150, 745.

EXAMPLE 32

2-(2-Homopiperidinethoxy)ethyl 2-(7-chloro-4-quinolyl)aminobenzoate

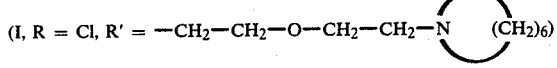

(I, R = Cl, R' = —CH$_2$—CH$_2$—O—CH$_2$—CH$_2$—N (CH$_2$)$_6$)

(A) 2-(2-Homopiperidinethoxy)ethyl antranilate (V, n=1, m=6):

5.64 g of isatoic anhydride are reacted with 5.02 g of 2-(2-homopiperidinethoxy)ethanol in 100 ml of toluene. 6.96 g (yield: 85%) of a yellow oil are isolated according to Example 22; n$_D^{20}$=1.5505, analysis elemental of C, H, N correct.

IR Spectrum (film), cm$^{-1}$: 3450, 3360, 3000-2660, 1680, 1610, 1580, 1480, 1290, 1240, 1150, 1110, 745.

(B) Reaction of 4,7-dichloroquinoleine (VI, R=Cl):

By treating 2-(2-homopiperidinethoxy)ethyl antranilate (6.12 g) as described above, and 4,7-dichloroquinoleine (5.07 g) as described in Example 28, it is obtained a solid (yield: 51%); m.p. 62°-64° C. and elemental analysis correct.

IR Spectrum (KBr), cm$^{-1}$: 3240, 3000-2700, 1675, 1600, 1570, 1520, 1445, 1245, 1080, 875, 740.

EXAMPLE 33

2-(2-Homopiperidinethoxy)ethyl 2-(7-trifluoromethyl-4-quinolyl)aminobenzoate (I, R=CF$_3$, n=1, m=6)

By treating 2-(2-homopiperidinethoxy)ethyl antranilate (6.12 g) as described in Example 32, and 4-chloro-7-trifluoromethylquinoleine (5.92 g) as described in above examples, 4.51 g (yield: 45%) are obtained; m.p. 53°-56° C. and elemental analysis correct.

IR Spectrum (KBr), cm$^{-1}$: 3260, 3000-2700, 1670, 1595, 1580, 1520, 1445, 1375, 1315, 1240, 1155, 1105, 740.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. 2-Pyrrolidinylethyl-2-(7-trifluoromethyl-4-quinolyl-aminobenzoate or a pharmacologically acceptacle acid addition salt thereof.

2. A pharmaceutical composition having analgesic, antipyretic and anti-inflammatory activities which comprises a therapeutically effective amount of a compound according to claim 1 and a pharmaceutically acceptable carrier thereof.

* * * * *